United States Patent
Puolakanaho et al.

(10) Patent No.: US 6,418,394 B1
(45) Date of Patent: Jul. 9, 2002

(54) MEASURING DEVICE AND METHOD OF CONTROLLING SAME

(75) Inventors: Pertti Puolakanaho, Oulu; Erkki Loponen, Ruukki; Pekka Rytky, Oulu, all of (FI)

(73) Assignee: Polar Electro Oy, Kempele (FI)

( * ) Notice: Subject to any disclaimer, the term of this patent is extended or adjusted under 35 U.S.C. 154(b) by 0 days.

(21) Appl. No.: 09/403,668

(22) Filed: Oct. 25, 1999

(30) Foreign Application Priority Data

May 21, 1997 (FI) .................................................. 972174

(51) Int. Cl.$^7$ .............................................. A61B 5/044
(52) U.S. Cl. ........................................ 702/139; 600/523
(58) Field of Search ............................ 702/33, 19, 41, 702/44, 108, 113, 127, 139, 175, 61, 176–178, 182–183, 187–188, 42, FOR 115, FOR 123, FOR 124, FOR 126, FOR 129, FOR 130, FOR 134, FOR 135, FOR 141, FOR 143, FOR 151, FOR 152, FOR 155, FOR 170; 600/523, 519, 521, 412; 607/122, 4, 17; 368/189; 377/20; 340/870.31

(56) References Cited

U.S. PATENT DOCUMENTS

| | | | | |
|---|---|---|---|---|
| 4,337,529 A | * | 6/1982 | Morokawa | 377/20 |
| 4,625,733 A | | 12/1986 | Säynäjäkangas | 600/500 |
| 4,798,206 A | * | 1/1989 | Maddison et al. | 607/122 |
| 5,007,429 A | | 4/1991 | Treatch et al. | 600/490 |
| 5,207,222 A | * | 5/1993 | Koizumi et al. | 600/412 |
| 5,261,042 A | | 11/1993 | Brandt | 345/841 |
| 5,477,508 A | * | 12/1995 | Will | 308/189 |
| 5,486,818 A | * | 1/1996 | Loponen | 340/870.31 |
| 5,538,007 A | * | 7/1996 | Gorman | 600/523 |
| 5,539,530 A | | 7/1996 | Reifman et al. | 358/402 |
| 5,586,067 A | * | 12/1996 | Gross et al. | 702/139 |
| 5,738,104 A | * | 4/1998 | Lo et al. | 600/521 |
| 5,824,014 A | * | 10/1998 | Thong et al. | 607/4 |
| 5,846,134 A | * | 12/1998 | Thong et al. | 607/17 |
| 5,876,350 A | * | 3/1999 | Lo et al. | 600/519 |
| 6,075,519 A | * | 6/2000 | Okatani et al. | 345/173 |

FOREIGN PATENT DOCUMENTS

| | | |
|---|---|---|
| CA | 2061027 | 9/1999 |
| EP | 0 623 870 A3 | 9/1996 |
| FI | 87871 | 12/1991 |
| FI | 88972 | 1/1993 |
| FI | 92782 | 8/1994 |
| FI | 93597 | 12/1994 |

\* cited by examiner

*Primary Examiner*—Marc S. Hoff
*Assistant Examiner*—Edward Raymond
(74) *Attorney, Agent, or Firm*—Hoffmann & Baron, LLP

(57) ABSTRACT

The invention relates to a measuring device (102) carried by a user during exercise for measuring non-invasively at least one signal from the body, e.g. a wireless heart rate monitor, and to a method of controlling same. The measuring device comprises a user interface (120). The user interface comprises selection means (114), e.g. push buttons (114), and display means (116,122), e.g. a liquid crystal display. The user interface (116) displays different operating modes, e.g., a watch mode (300), a set mode (306) and an operating mode (302) for measuring a signal from the body. The operating modes have different sub-operating modes for displaying parameter associated with exercising. In accordance with the invention, the user is shown specified operating modes and sub-operating modes. There is also a special help operating mode, which, when being switched on, allows each selection means available in said operating mode or sub-operating mode to be indicated to the user by automatic stepping, and the function to be performed by selecting said selection means to be specified.

36 Claims, 8 Drawing Sheets

MEASURING DEVICE AND METHOD OF CONTROLLING SAME

FIELD OF THE INVENTION

The invention relates to a measuring device carried by a user during exercise for measuring non-invasively at least one signal from the body, the measuring device comprising
- a measuring unit for measuring at least one signal from the body,
- a user interface comprising selection means for making selections, and display means for displaying data,
- a control unit communicating with the measuring unit and the user interface for controlling and monitoring the operation of the measuring device,
- various operating modes comprising at least a watch mode, a set mode, and at least one operating mode for measuring a signal from the body,
- the operating modes comprising various sub-operating modes for displaying parameters associated with exercising.

DESCRIPTION OF RELATED ART

Various portable personal measuring devices for measuring a signal of the user's choice from the body have been designed during the last few years. Devices have been designed for different end users: persons concerned with their health, fitness enthusiasts, goal-oriented athletes and sports champions.

Signals to be measured include e.g. heart rate and arterial blood pressure. These measurements can be carried out non-invasively, i.e. the measuring sensors are disposed on a person's skin. Hence the use of meters is safe and suitable for everyone.

A measuring device designed for measuring heart rate, i.e. a heart rate monitor, for example, is employed to improve physical and mental condition efficiently and safely. The user can employ a heart rate monitor to monitor his heart rate level during exercising, for example, and avoid excessive stress. A heart rate monitor can also be utilized in slimming since it has been scientifically shown that the most efficient way to burn fat stored in the body is to exercise at a given heart rate (about 55 to 65% of a person's maximum heart rate. The maximum heart rate is calculated e.g. by subtracting the person's age from 220, or the maximum heart rate can also be measured.).

In U.S. Pat. No. 4,625,733 Saynajakangas teaches a wireless and continuous heart rate measuring concept employing a transmitter attached to a user's chest for ECG accurate measuring of the user's heart rate and for telemetric transfer of heart rate data to a heart rate receiver attached to the user's wrist by employing magnetic coils in the transfer.

In addition to a receiver, the unit attached to the wrist comprises a control unit and a user interface. The control unit controls and monitors the operation of the measuring device. The necessary heart rate data processing is also carried out in the control unit. The control unit is typically a microprocessor also comprising an ROM memory in which the software of the measuring device is stored. The control unit can also comprise separate memory in which measurement data generated during the use of the device can be stored for further processing. For further processing, the data can be transferred to a separate personal computer.

The user interface of a heart rate monitor comprises selection means for making selections, and display means for displaying data. The selection means are typically push buttons. The number of buttons may vary, typically totalling three separate buttons. In addition, a so-called wireless button can be used. This means that the user selects the desired function, e.g. the start of measurement, by a special operation, e.g. by bringing the transmitter and the receiver close to one another. This closeness is detected in the magnetic coils on account of the changes which their closeness causes in the magnetic field. A conventional liquid crystal display typically serves as the display means.

The user operates the heart rate monitor by pressing the buttons. The heart rate monitor provides feedback on its display as text, numbers and various symbols.

The basic structure of the user interface in nearly all known heart rate monitors comprises different operating modes. A heart rate monitor usually comprises at least a watch mode and a heart rate measurement mode. In watch mode the heart rate monitor operates as a normal wrist watch. An operating mode may also have sub-operating modes somehow associated with the operating mode. In sub-operating modes, different parameters associated with exercising are displayed to the user. The time of day is a parameter indicating real exercise time. The date can also be displayed. An alarm clock type of sub-operating mode is also common.

Different parameters measured for the exercise are displayed In heart rate measurement mode. Examples of sub-operating modes are e.g. exercise time and heart rate, real exercise time and heart rate, effective exercise time and heart rate, energy consumed by the user in the exercise and heart rate. In heart rate measurement mode the user can also be controlled by means of sound signals and symbols displayed on the display. The control may aim at keeping the exercise within effective and safe limits (typically within the range 55 to 85% of a person's maximum heart rate). In this case the user himself typically sets the lower and upper limits for his heart rate. The limits are established on the basis of information obtained in medical studies. During exercise, the measuring device gives an alarm if the heart rate exceeds the upper limit or falls below the lower limit.

The operating modes often also comprise a set mode. The set mode allows the user to set functions controlling and facilitating the exercise, e.g. said lower and upper limits for the heart rate.

The operating modes may also comprise a file mode. This is subject to the device comprising memory for storing data during exercise in the manner described above. In file mode the stored data can be studied and analyzed later.

The described device to be attached to the wrist is small, which limits the size of the buttons and the display. However, the data displayed on the display have to be presented by large enough letters, numbers or symbols to allow easy detection thereof by the main user groups of the device. When running, for example, the user has to be able to swiftly perceive the information on the display, often for traffic safety reasons alone. The effectiveness of the exercise falls if the user has to interrupt the exercise in order to use the device, since the heart rate starts to fall when the user is standing still. This is why the display should not show too much information at the same time.

Another problem is associated with the buttons. The sizes of the buttons have to be sufficient for example for a skier wearing ski gloves to be able to operate the device. Neither should there be too many buttons, since the user may have difficulty in learning their operation.

The user interface employs symbolics and a complex operating logic, the learning of which requires of the user high motivation and that he acquaint himself with the operator's manual.

When using the device, the user is typically engaged in an exercise of the duration of perhaps several hours, and is not necessarily carrying the manual with him. If a problem arises, the user may be frustrated, in the worst case the stored measurement results may even be lost because of faulty operation of the device by the user.

Although the device in itself, objectively assessed, seems easy to use, the above reasons may have made it tedious and difficult for the user to learn to operate the device and form an internal model in his mind for the use of the device.

CHARACTERISTICS OF THE INVENTION

It is the object of the present invention to provide a measuring device of the type described, the use of which is easier to learn than that of present measuring devices. The invention particularly relates to the user interface of the measuring device.

This is achieved by a measuring device of the type described in the introduction, characterized by the control unit being adapted to specify the operating modes and sub-operating modes and display them by the display means, and by the measuring device comprising a help operating mode, the control unit, when the help operating mode is switched on, being adapted to indicate by the display means, using automatic stepping, alternately each selection means in that particular operating mode or sub-operating mode and to specify the function to be performed by selecting said selection means.

The invention further relates to a method of controlling a measuring device carried by a user during exercise for measuring non-invasively at least one signal from the body, the measuring device comprising a measuring unit for measuring at least one signal from the body, a user interface comprising selection means for making selections, and display means for displaying data, a control unit communicating with the measuring unit and the user interface for controlling and monitoring the operation of the measuring device, various operating modes comprising at least a watch mode, a set mode, and at least one operating mode for measuring a signal from the body, the operating modes comprising various sub-operating modes for displaying parameters associated with exercising.

In accordance with the invention, the method is characterized by specifying the operating modes and sub-operating modes and displaying them by the display means to the user, and by the measuring device comprising a help operating mode, the display means, when the help operating mode is switched on, indicating alternately, using automatic stepping, each selection means in that particular operating mode or sub-operating mode and specifying the operation to be performed by selecting said selection means.

The method and measuring device of the invention provide significant advantages. It is easier and faster for a user to learn how to operate the device. Learning takes place by experimenting, minimizing the need of a separate operator's manual. Furthermore, the user is automatically supplied with help if problems arise. Having learned how to operate the device, the user may switch off the help operating mode.

DESCRIPTION OF THE DRAWINGS

In the following the invention will be described in greater detail with reference to examples according to the attached drawings, in which.

DESCRIPTION OF THE PREFERRED EMBODIMENTS

The present invention is suitable for use in all types of measuring devices, which are carried by a user during exercise for measuring non-invasively at least one signal from the body, in e.g. heart rate monitors, and even in advanced versions of heart rate monitors in which e.g. the user's energy consumption, blood pressure etc. are measured in addition to or instead of the heart rate. In principle the described help function can be implemented in any electronic device comprising a similar interface.

Figure 1B:
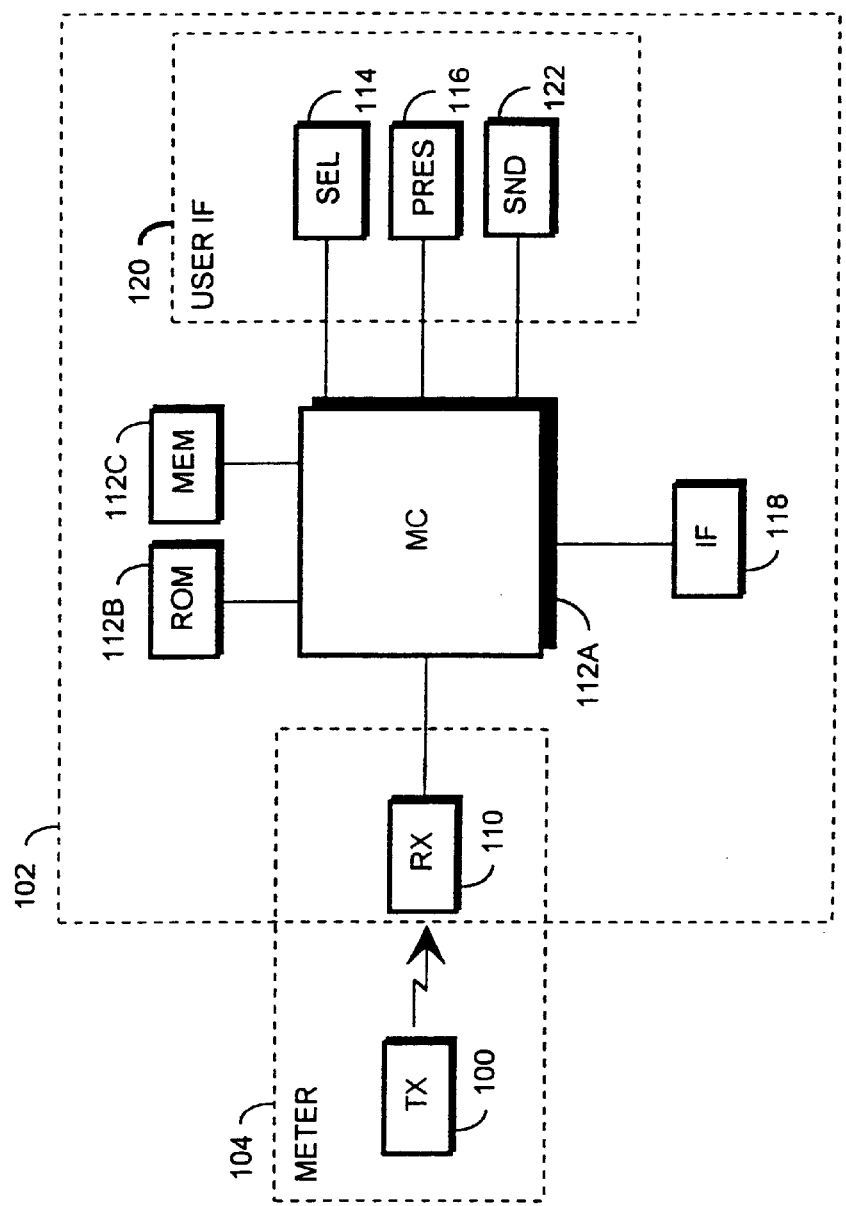
FIG. 1B is a block diagram of a more detailed structure of a measuring device.
Figure 1A:
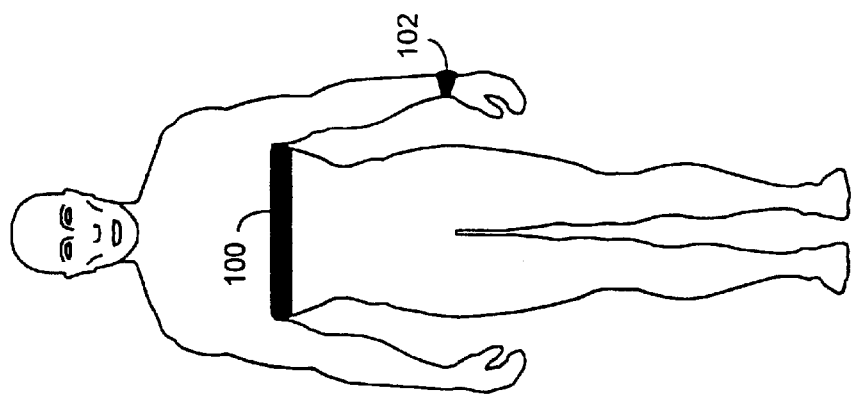
FIG. 1A shows how a user typically carries a measuring device with himself.

FIGS. 1A and 1B illustrate a preferred embodiment of the present invention, a heart rate monitor. A heart rate monitor 102 typically comprises a measuring unit 104 and a control unit 112A controlling the measuring unit. The control unit 112A also controls a user interface 120 comprising selection means 114 and display means 116. The control unit 112A is typically a microprocessor comprising an ROM memory 112B in which the software controlling the device is stored. The device may further comprise additional memory 112C, in which information on e.g. heart rate, gathered during the measurement, can be stored. In principle the control unit can also be implemented by an ASIC circuit or by another coupling composed of HW units. Thus the changes according to the invention in the measuring device are preferably changes in the software of the device.

The measuring unit 104 may be one piece, e.g. a heart rate monitor carried on the wrist, the heart rate being measured from the wrist. However, a better measurement result is obtained by present technology by using a solution of the type described, in which the measuring unit 104 is divided into two parts: a wireless transmitter 100 that is attached around the chest and measures the heart rate, and a heart rate receiver 110 attached to the wrist.

Figure 2:
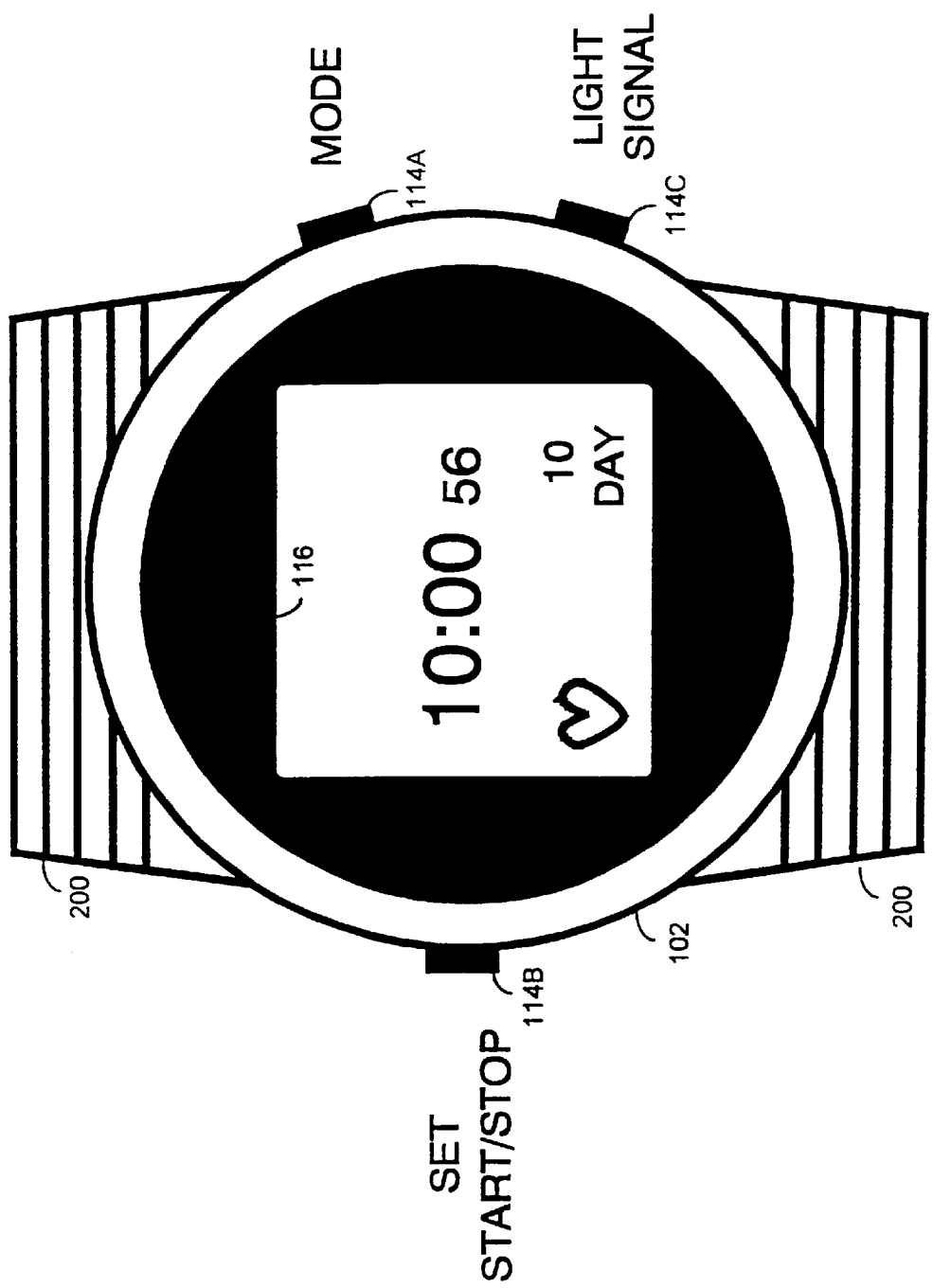
FIG. 2 shows a typical user interface of a measuring device.

FIG. 2 shows a typical heart rate monitor user interface. A wrist watch type of heart rate monitor 102 is attached to a wristband 200. A liquid crystal display 116 is used as the display means. In the figure, the liquid crystal display 116 displays in watch mode the time of day, 10:00.56, and the day of month, 10. The display also displays a heart symbol for indicating whether heart rate measurement is active. The three push buttons 114A, 114B and 114C shown in the figure constitute the selection means. Button 114A (MODE) is intended for shifting between the different modes and displays. Button 114B (SET, START/STOP) is used for making selections and for starting and stopping functions. Button 114C (LIGHT, SIGNAL) is intended for adjusting the settings and for using the background light of the display 116 and the sound signal during the measurement function.

In addition a wireless button can be used which is based on magnetic induction and is activated by bringing close to each other the heart rate receiver 110 comprised by the heart rate monitor 102 and the transmitter 110 to be attached around the chest. The operating principle is described in greater detail in U.S. Pat. No. 5,486,818. By the operation of the wireless button it is possible e.g. to display an additional display or switch on the background light illuminating the display 116 in measurement mode.

The measuring device may allow the user e.g. to program a short-cut function for a selection means in set mode. This short-cut allows the user to rapidly access a frequently used function, e.g. a sub-operating mode.

Another feature facilitating the use is a home selection function. This home option function allows the user to rapidly access the basic mode of the device, e.g. watch mode. Both the short-cut and home selection can be implemented in various ways. An alternative is to simultaneously press several selection means, e.g. two different buttons, to make the selection. Another alternative is to press the button for a long time, e.g. two seconds, after which the selection is made.

The user interface also comprises a sound signal indicating e.g. an alarm, exceeding or falling below the set heart rate limit, or other information relevant to the user. To produce a sound signal, the heart rate monitor 102 comprises a sound unit 122.

The heart rate monitor 102 frequently comprises an interface 118 between the heart rate monitor 102 and the outside world. Information stored in the heart rate monitor can be transferred via the interface 118 to e.g. a personal computer for further processing. The heart rate monitor software can also be updated via the interface 118. This calls for special mechanisms, e.g. the ROM memory 112B in which the software is stored has to be replaced by a write-enable type of memory.

Figure 3:
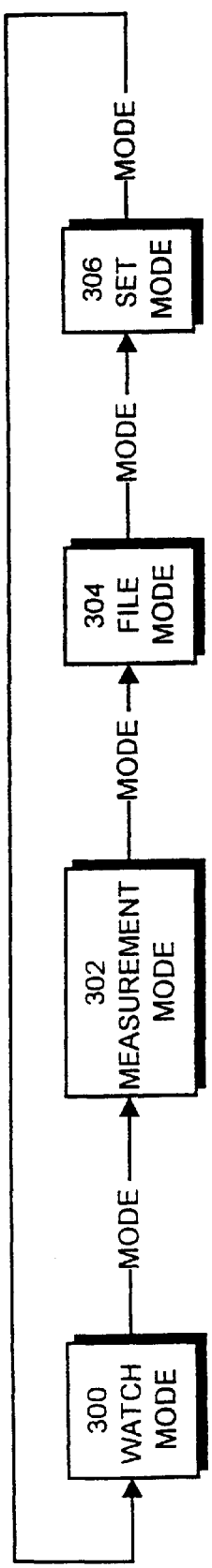
FIG. 3 shows operating modes and shifting between them.

FIG. 3 shows a way to implement the grouping of the operating mode: they form a main loop sequence. The user of the heart rate monitor 102 sees the details associated with each operating mode on the display 116. The heart rate monitor 102 typically comprises at least the first two of the following operating modes: a watch mode 300, a heart rate measurement mode 302, a file mode 304 and a set mode 306. As is also shown in FIG. 3, button 114A (MODE) has to be pressed to shift from one operating mode to another. When the user sees the watch mode 300 on the display 116, he can press the MODE button 114A once to access the heart rate measurement mode 302. Thus, pressing the MODE button 114A allows the user to advance in one direction in the main loop sequence. From the last set operating mode 306 of the main loop sequence, the user again reaches the start, the watch mode 300, by pressing the MODE button 114A.

Figure 4A:
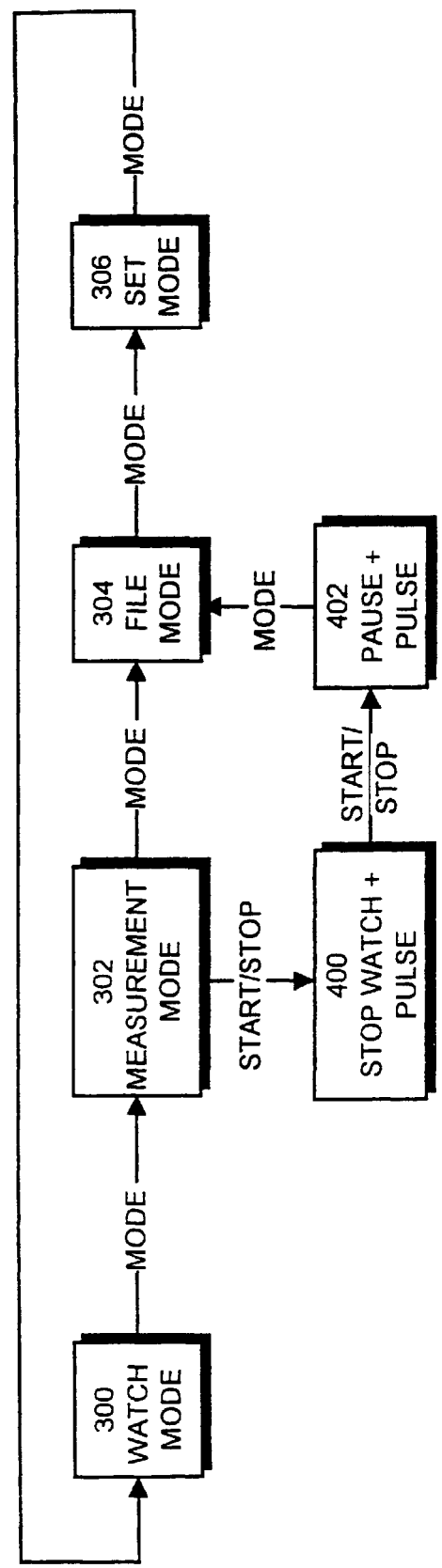
FIG. 4A shows heart rate measurement at its simplest.

FIG. 4A shows how a user, when employing the heart rate monitor 102, typically shifts from one operating mode to another. The user is first in the watch mode 300. The user wants to start an exercise, e.g. a run, and consequently presses once the MODE button 114A to access the heart rate measurement mode 302. Having accessed the heart rate measurement mode 302, the user presses the START/STOP button 114B to access the first sub-operating mode 400 of the sub-loop sequence of the heart rate measurement mode 302, displaying exercise time and user heart rate. Having run a while, the user wants to stop the exercise, and consequently presses the START/STOP button 114B again. This gains access to a sub-operating mode 402 of the sub-loop sequence of the heart rate measurement mode 302, displaying exercise time and user heart rate. By pressing the START/STOP button 114B again, the user may continue the exercise, or shift by the MODE button 114A to the next operating mode of the main loop sequence, i.e. the file mode 304.

Figure 4B:
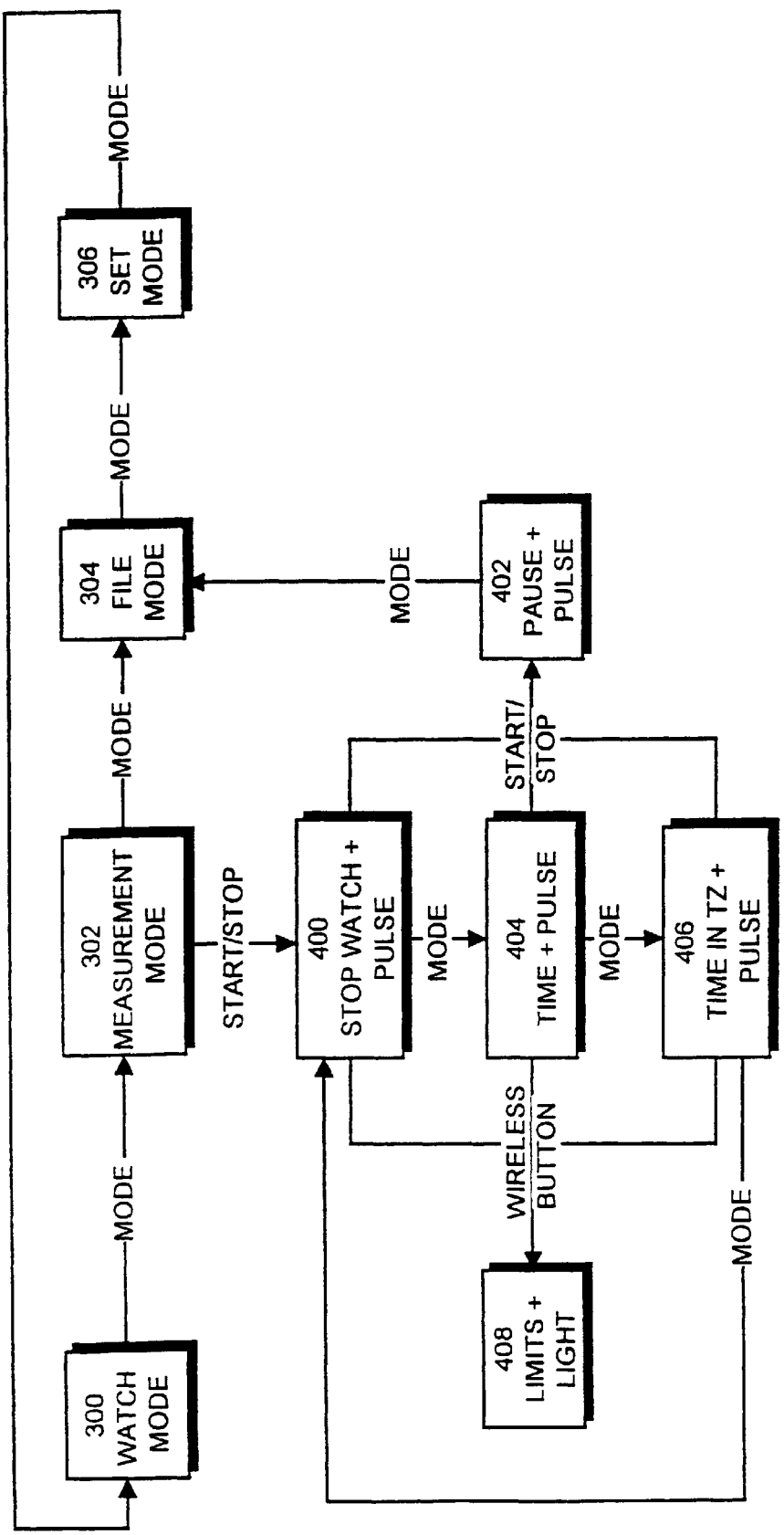
FIG. 4B shows more advanced user heart rate measurement.

FIG. 4B shows how a more experienced user may use the device in a more versatile manner compared with the basic functions of a novice described in FIG. 4A. Thus the user may advance during measurement along the sub-loop sequence of the heart rate measurement mode 302 by pressing the MODE button 114A. The sub-operating mode 404 displays real exercise time and heart rate. The sub-operating mode 406 displays effective exercise time and heart rate. During measurement, access can be gained by the wireless button to the sub-operating mode 408 which displays the set heart rate limits, and allows the background light of the display 116 to be switched on.

Figure 6C:
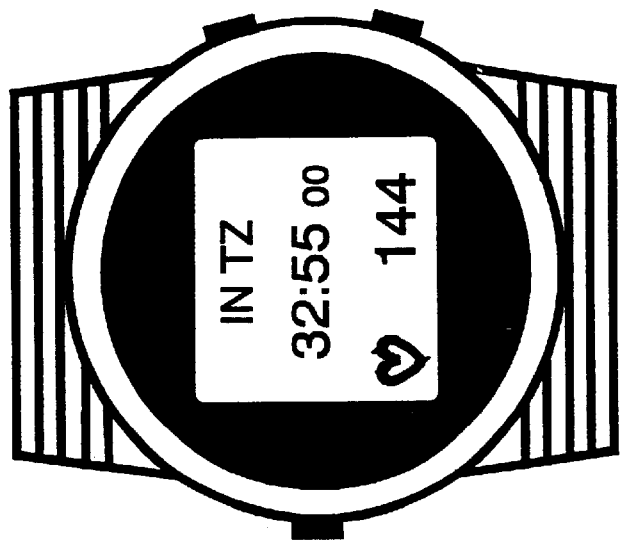
FIGS. 6A, 6B and 6C show how the sub-operating modes are specified.

In accordance with the invention, the operating modes and sub-operating modes have been specified, and each mode title is displayed by the display means in order for the user to know in which mode the meter is. In the example of FIG. 4B, the information displayed to the user by the display means 116 in the sub-operating mode 400 is as shown in FIG. 6A. The top of the display 116 displays the sub-operating mode title, STOPW (timing), 45:00.00 being the total time taken up by the exercise, 143 is the current pulse, and the heart-shaped symbol indicates that heart rate measurement is switched on.

Figure 6B:
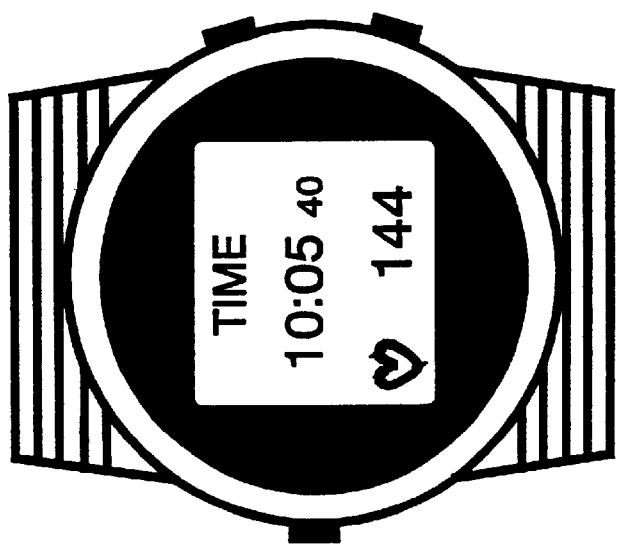
Figure 6A:
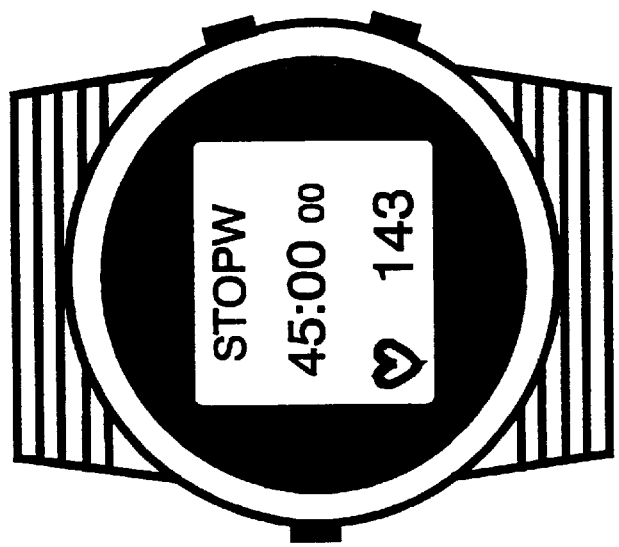

FIG. 6B shows the display of the next sub-operating mode 404. Again the top of the display 116 displays the sub-operating mode title, TIME, 10:05.40 being real exercise time, i.e. current time of day, 144 is the current pulse, and the heart-shaped symbol indicates that heart rate measurement is switched on.

FIG. 6C shows the display of the last sub-operating mode 406. Again the top of the display 116 displays the sub-operating mode title, IN TZ (effective exercise time), 32:55.00 being the time during which the user's pulse has been above the lower limit of the heart rate, 144 is the current pulse, and the heart-shaped symbol indicates that heart rate measurement is switched on.

In accordance with the invention the measuring device comprises a help operating mode, the control unit, when the help operating mode is switched on, being adapted to indicate by the display means, using automatic stepping, alternately each selection means in that particular operating mode or sub-operating mode and to specify the function to be performed by selecting said selection means. Let us study FIG. 7A, which shows the first display of the set mode 306. The operating mode is named SET in order for the user to know which operating mode is active.

If the user does nothing e.g. within 3 to 6 seconds, help is initiated. In accordance with FIG. 7B, an indicator means, in this case an arrow-shaped cursor, is used to indicate the SET button 114B, the text START indicating that setting will start if said button is pressed. Display time is such that the user has time to detect the function title and the selection means with which said function is to be selected. Display time is preferably 2 to 4 seconds.

Figure 7C:
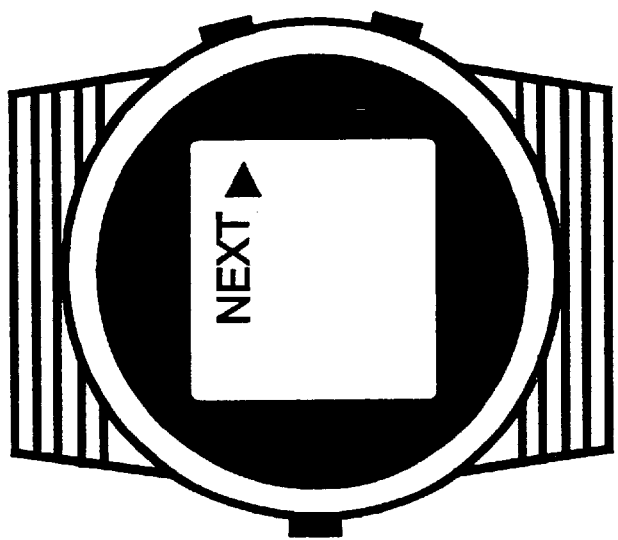
FIGS. 7A to 7F show how help operates.
Figure 7B:
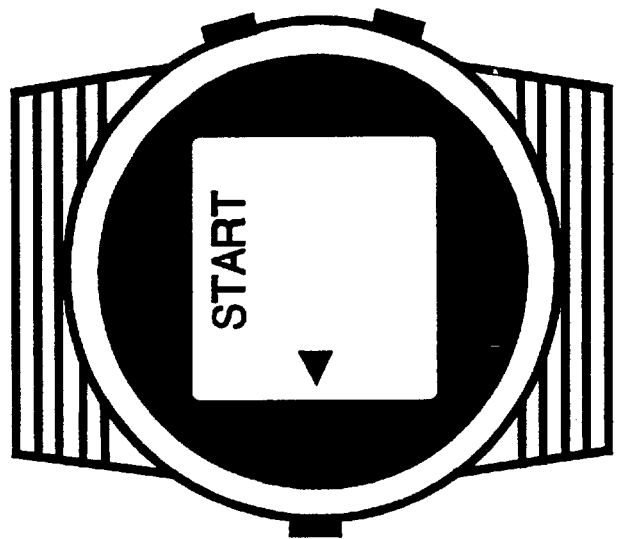
Figure 7A:
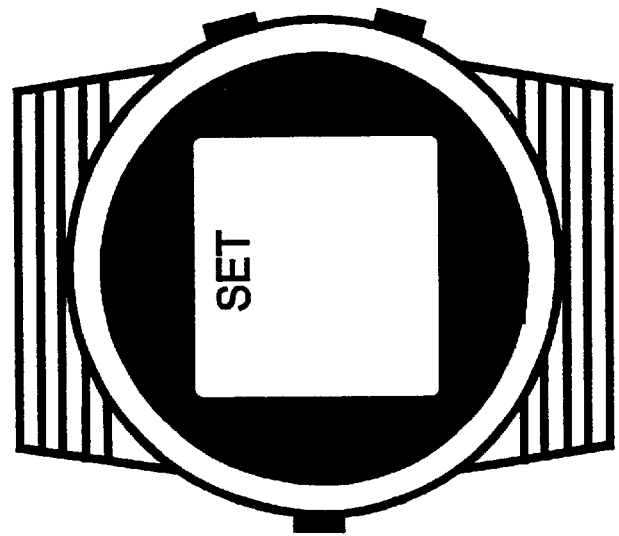

A display as shown in FIG. 7C is then displayed, in which an arrow is used to indicate the MODE button 114A, the text NEXT indicating that if said button is pressed, access will be gained to the following operating mode, i.e. the watch mode 300.

The indicator means can also be implemented in other ways, and its shape on the display may also be different. Another solution is to carry out the indication by using the background light illuminating said selection means.

Automatic stepping can involve an automatically repeated loop sequence. In other words, once the selection means available in said operating mode or sub-operating mode have been indicated to the user, a pause follows and the selection means are then indicated again.

In certain operating modes, e.g. in the measurement mode 302, help is not necessarily in use since an exercise may last for hours, and there is no point in supplying the user with help continuously every few seconds. In other words, the help operating mode is most advantageous in association with less frequently used functions.

If needed, the help mode can be switched off, e.g. once the user has become familiar with the use of the device and no longer needs help.

Figure 5:
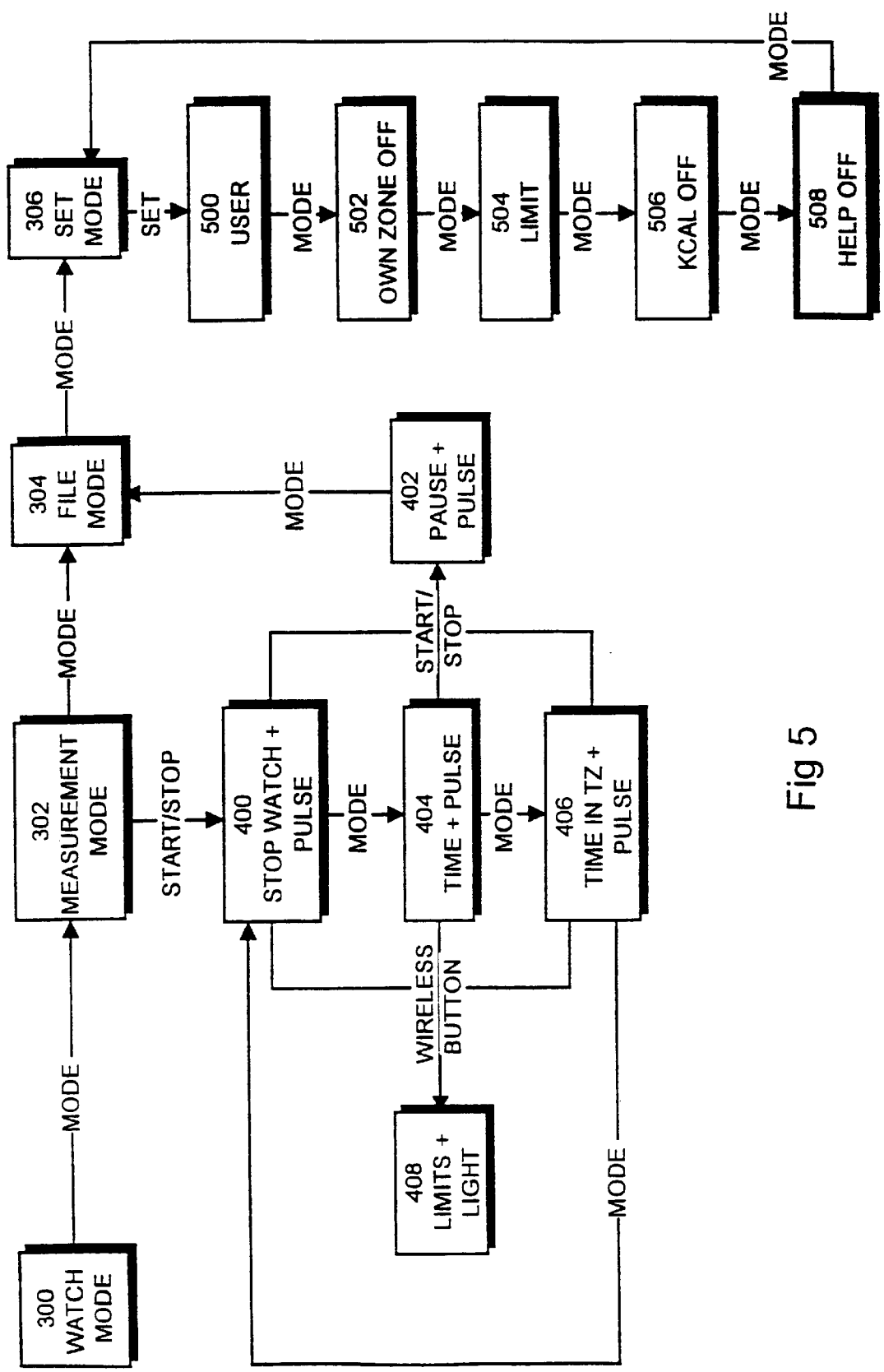
FIG. 5 shows how the operation of the help operating mode is controlled.
Figure 7F:
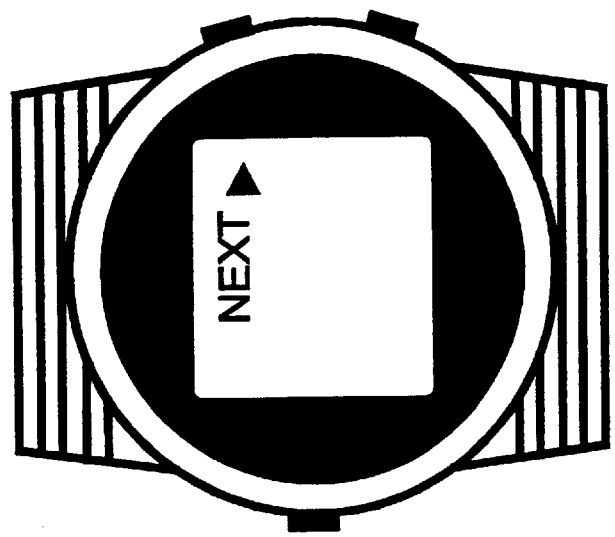
Figure 7E:
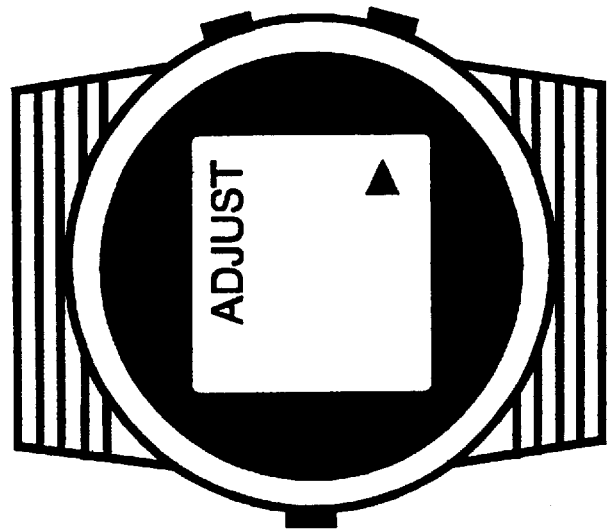
Figure 7D:
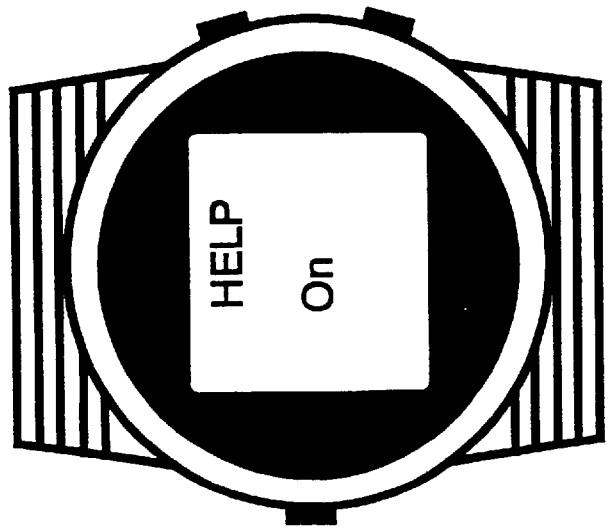

FIG. 5 shows an example of how configuration is carried out. In the operating modes the MODE button 114A is pressed to access the set mode 306, in which the change of settings is initiated by pressing the SET button 114B. User-specific settings 500 (e.g. age, weight and sex) are first accessed and bypassed by pressing the MODE button 114A. The sub-operating modes automatic setting of heart rate limits 502, limits to be set 504, and calculation of energy consumed by the user 506, are also bypassed without any changes in the settings. In accordance with FIG. 7D, the user is displayed the plain text name HELP of the help operating mode 508 and the current setting On. In the sub-operating mode 508 the help mode can be switched on or off by pressing the SET button 114B. When the help operating mode is on, help displays according to FIGS. 7E and 7F are displayed to the user unless he makes a selection in e.g. 3 to 6 seconds. The user exits the set mode sub-loop sequence by pressing the MODE button 114A once more.

Although the invention is described herein with reference to the example in accordance with the accompanying drawings, it will be appreciated that the invention is not to be so limited, but may be modified in a variety of ways within the scope of the inventive idea disclosed in the appended claims.

What is claimed is:

1. A measuring device carried by a user during exercise for measuring non-invasively at least one signal from the body, the measuring device comprising:
    a control unit for controlling and monitoring the operation of the measuring device;
    a measuring unit communicating with the control unit for measuring at least one signal from the body;
    a user interface communicating with the control unit, comprising:
       selection means for making selections;
       various operating modes comprising at least a watch mode, a set mode, and at least one operating mode for measuring a signal from the body, the operating modes comprising various sub-operating modes for displaying parameters associated with exercising; and
       display means for displaying data to the user, the control unit being adapted to specify the operating modes and sub-operating modes and display them by the display means, the measuring device comprising a help operating mode, the control unit, when the help operating mode is switched on, being adapted to indicate, by the display means, using automatic stepping, alternately, each selection means in that particular operating mode or sub-operating mode and to specify the function to be performed by selecting said selection means.

2. A measuring device as claimed in claim 1, wherein the control unit is adapted to receive a selection made by the selection means during the automatic stepping.

3. A measuring device as claimed in claim 1, wherein the control unit is adapted to display the help text always in the same place, the help text specifying the function to be performed.

4. A measuring device as claimed in claim 1, wherein the selection means are at least one of operating mode specific and sub-operating mode specific.

5. A measuring device as claimed in claim 1, wherein the display means are adapted to carry out the indication by an indicator means.

6. A measuring device as claimed in claim 5, wherein the indicator means include an arrow-shaped cursor.

7. A measuring device as claimed in claim 5, wherein the indicator means include a background light illuminating said selection means.

8. A measuring device as claimed in claim 1, wherein the control unit is adapted to operate in such a way that, in set mode, the help operating mode can be switched off.

9. A measuring device as claimed in claim 1, wherein the control unit is adapted to initiate indication if the user fails to make the selection required in said operating mode.

10. A measuring device as claimed in claim 9, wherein the user has about 3 to 6 seconds to make the required selection before indication is initiated.

11. A measuring device as claimed in claim 1, wherein when stepping, the control unit is adapted to display each function for such a duration that the user has time to detect the function title and the selection means for selecting said function within said time.

12. A measuring device as claimed in claim 11, wherein the display time is between about 2 and 4 seconds.

13. A measuring device as claimed in claim 1, wherein the automatic stepping includes an automatically repeated loop sequence.

14. A measuring device as claimed in claim 1, wherein the selection means include push buttons.

15. A measuring device as claimed in claim 1, wherein the display means include a liquid crystal display.

16. A measuring device as claimed in claim 15, wherein the liquid crystal display includes a dot matrix liquid crystal display.

17. A measuring device as claimed in claim 1, wherein the signal to be measured is a user heart rate, the operating mode measuring the signal from the body is a heart rate measurement mode, and the measuring device is a heart rate monitor.

18. A measuring device as claimed in claim 17, wherein the measuring unit comprises a wireless transmitter to be attached to the chest and a wireless heart rate receiver attached to the wrist.

19. A method of controlling a measuring device carried by a user during exercise for measuring non-invasively at least one signal from the body, the measuring device comprising:
    a control unit for controlling and monitoring the operation of the measuring device;
    a measuring unit communicating with the control unit for measuring at least one signal from the body;
    a user interface communicating with the control unit, comprising:
       selection means for making selections;
       various operating modes comprising at least a watch mode, a set mode, and at least one operating mode for measuring a signal from the body, the operating modes comprising various sub-operating modes for displaying parameters associated with exercising; and display means for displaying data to the user, the control unit being adapted to specify the operating modes and sub-operating modes and displaying them by the display means to the user, the measuring device comprising a help operating mode, the method comprising the steps of:

indicating, by the display means, when the help operating mode is switched on, alternately, using automatic stepping, each selection means in that particular operating mode or sub-operating mode; and specifying the operation to be performed by selecting said selection means.

20. A method as claimed in claim 19, further comprising the step of receiving, by the control unit, a selection made by the selection means during the automatic stepping.

21. A method as claimed in claim 19, further comprising the step of displaying the help text always in the same place, the help text specifying the function to be performed.

22. A method as claimed in claim 19, further comprising the step of specifying the function of the selection means as being at least one of operating mode specific and sub-operating mode specific.

23. A method as claimed in claim 19, wherein the display means are adapted to carry out the indication by an indicator means.

24. A method as claimed in claim 23, wherein the indicator means include an arrow-shaped cursor.

25. A method as claimed in claim 23, wherein the indicator means include a background light illuminating said selection means.

26. A method as claimed in claim 19, further comprising the step of enabling, in set mode, the help operating mode to be switched off.

27. A method as claimed in claim 19, further comprising the step of initiating indication if the user fails to make the selection required in said operating mode.

28. A method as claimed in claim 27, further comprising the step of initiating indication about 3 to 6 seconds after the user makes the required selection.

29. A method as claimed in claim 19, further comprising the step of displaying, when stepping each function, for such a duration that the user has time to detect the function title and the selection means for selecting said function within said time.

30. A method as claimed in claim 29, wherein the display time is between about 2 and 4 seconds.

31. A method as claimed in claim 19, wherein the automatic stepping includes an automatically repeated loop sequence.

32. A method as claimed in claim 19, wherein the selection means include push buttons.

33. A method as claimed in claim 19, wherein the display means include a liquid crystal display.

34. A method as claimed in claim 33, wherein the liquid crystal display includes a dot matrix liquid crystal display.

35. A method as claimed in claim 19, further comprising the step of measuring a user heart rate as the signal to be measured, the operating mode measuring the signal from the body being a heart rate measurement mode, and the measuring device being a heart rate monitor.

36. A method as claimed in claim 35, wherein the measuring unit comprises a wireless transmitter to be attached to the chest and a wireless heart rate receiver to be attached to the wrist.

* * * * *

UNITED STATES PATENT AND TRADEMARK OFFICE
CERTIFICATE OF CORRECTION

PATENT NO.    : 6,418,394 B1                                         Page 1 of 1
DATED         : July 9, 2002
INVENTOR(S)   : Puolakanaho et al.

It is certified that error appears in the above-identified patent and that said Letters Patent is hereby corrected as shown below:

<u>Title page,</u>
Item [22], Related U.S. Application Data, now reads "[22] Filed: Oct. 25, 1999" should read -- [22] PCT Filed: May 20, 1998 --

Please include the following information:
-- [86]  PCT No.:       PCT/FI98/00428
         §371 Date:     October 25, 1999
         § 10 2(e) Date: October 25, 1999
   [87]  PCT Pub. No.:  WO 98/55023
         PCT Pub. Date: December 10, 1998 --

Signed and Sealed this

Eighteenth Day of February, 2003

JAMES E. ROGAN
*Director of the United States Patent and Trademark Office*